United States Patent [19]

Hoffmann et al.

[11] 4,342,704
[45] Aug. 3, 1982

[54] PROCESS FOR THE PREPARATION OF 1,1-DICHLOROALKENES

[75] Inventors: Hellmut Hoffmann; Fritz Maurer, both of Wuppertal; Uwe Priesnitz, Unna-Massen; Hans-Jochem Riebel, Wuppertal, all of Fed. Rep. of Germany

[73] Assignee: Bayer Aktiengesellschaft, Leverkusen, Fed. Rep. of Germany

[21] Appl. No.: 165,872

[22] Filed: Jul. 2, 1980

[30] Foreign Application Priority Data

Jul. 21, 1979 [DE]  Fed. Rep. of Germany ....... 2929645

[51] Int. Cl.$^3$ ................. C07C 120/00; C07C 121/48; C07C 102/00; C07C 45/61
[52] U.S. Cl. ................................ 260/464; 260/938; 260/940; 260/946; 260/544 L; 560/124; 562/506; 564/190; 568/348; 570/193; 570/217; 570/237
[58] Field of Search .................. 570/193, 217, 237; 260/464; 568/347, 348; 564/190

[56] References Cited

U.S. PATENT DOCUMENTS

| 3,139,377 | 6/1964 | Ratts | 570/193 X |
| 3,247,265 | 4/1966 | Speziale et al. | 570/217 X |
| 3,247,266 | 4/1966 | Speziale et al. | 570/193 |
| 3,755,411 | 8/1973 | Henrick et al. | 570/217 X |

FOREIGN PATENT DOCUMENTS

| 2827101 | 6/1978 | Fed. Rep. of Germany . |
| 345 | 1/1979 | Fed. Rep. of Germany . |
| 2849 | 7/1979 | Fed. Rep. of Germany . |
| 11695 | 6/1980 | Fed. Rep. of Germany . |

OTHER PUBLICATIONS

Chemical Abstracts vol. 83, 1975, 192632r, Savignac, et al.
Chemical Abstracts vol. 80, 1974, 27328b, Seyferth, et al.
Fieser et al., Reagents for Organic Synthesis, vol. 1 (1967), pp. 223 and 250, John Wiley & Sons, N.Y.
Fieser et al., Reagents for Organic Synthesis, vol. 2 (1969), pp. 131-132 and 155, John Wiley & Sons, N.Y.
Fieser et al., Reagents for Organic Synthesis, vol. 3 (1972), p. 97, John Wiley & Sons, N.Y.
Fieser et al., Reagents for Organic Synthesis, vol. 4 (1974), pp. 150-151, John Wiley & Sons, N.Y.
Fieser et al., Reagents for Organic Synthesis, vol. 6 (1977), pp. 188, 189, 191, 193, John Wiley & Sons, N.Y.
Fieser et al., Reagents for Organic Synthesis, vol. 7 (1979), pp. 104, 106-107, 125-126, John Wiley & Sons, N.Y.
"The Merck Index", 8th ed. (1968), pp. 1226-1227.
Speziale et al., J.A.C.S., 84 (1962), pp. 854-859.

Primary Examiner—Joseph Paul Brust
Attorney, Agent, or Firm—Sprung, Horn, Kramer & Woods

[57] ABSTRACT

A process for the preparation of a 1,1-dichloroalkene of the formula $$\begin{array}{c} Cl \\ \phantom{Cl} \diagdown \\ \phantom{Cl} \phantom{\diagdown} C=C \\ \phantom{Cl} \diagup \phantom{C=C} \diagdown \\ Cl \phantom{\diagup C=C} R^2 \end{array} \begin{array}{c} R^1 \\ \end{array}$$

in which
  $R^1$ is hydrogen or an optionally substituted alkyl, alkenyl, alkynyl, aralkyl or aryl radical, and
  $R^2$ is an optionally substituted alkyl, alkenyl, alkynyl, aralkyl, aralkenyl or aryl radical, or cycloalkyl which is optionally substituted by halogen, alkyl, alkanoyl, carbamoyl, cyano or phenyl, or
  $R^1$ and $R^2$ together form a hydrocarbon chain which is optionally branched and/or optionally contains a fused benzene ring, comprising reacting an aldehyde or ketone of the formula $$O=C \diagdown_{R^2}^{R^1}$$

with a dichloromethane-phosphonic acid ester of the formula $$\begin{array}{c} O \phantom{xx} OR^3 \\ \parallel \diagup \\ Cl_2CH-P \\ \phantom{Cl_2CH-P} \diagdown \\ \phantom{Cl_2CH-P} OR^3 \end{array}$$

in which
  $R^3$ each independently is alkyl or phenyl or the two radicals $R^3$ together are alkanediyl, in the presence of a base at a temperature between about $-50°$ and $+50°$ C. Preferably either the base is metered into a mixture of the aldehyde or ketone and phosphonic acid ester or the ester is added to a mixture of the base and aldehyde or ketone.

8 Claims, No Drawings

PROCESS FOR THE PREPARATION OF 1,1-DICHLOROALKENES

The invention relates to an unobvious process for the preparation of certain 1,1-dichloro-alkenes.

It is known that such 1,1-dichloroalkenes as 3-(2,2-dichloro-vinyl)-2,2-dimethyl-cyclopropane-1-carboxylic acid tert.-butyl ester are obtained when such aldehydes as 3-formyl-2,2-dimethyl-cyclopropane-1-carboxylic acid tert.-butyl ester are reacted with triphenylphosphine in carbon tetrachloride (see DE-OS (German Published Specification) No. 2,326,077). However, the desired products are only obtained in moderate yields by this synthesis method.

It is further known that 1,1-dichloro-alkenes are obtained when lithium salts of dichloromethane-phosphonic acid esters are reacted with aldehydes or ketones (see Synthesis 1975, 535–536).

However, the preparation of the lithium salts of dichloromethane-phosphonic acid esters is relatively expensive; they are obtained from chloromethane-phosphonic acid esters by reaction with butyl-lithium and carbon tetrachloride at −75° C., for which carefully dried solvents must be used and an inert gas atmosphere is required.

The present invention now provides a process for the preparation of a 1,1-dichloro-alkene of the general formula

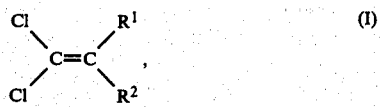

in which $R^1$ represents hydrogen or an optionally substituted alkyl, alkenyl, alkynyl, aralkyl or aryl radical and $R^2$ represents an optionally substituted alkyl, alkenyl, alkynyl, aralkyl, aralkenyl or aryl radical or cycloalkyl which is optionally substituted by halogen, alkyl, alkanoyl, carbamoyl, cyano or phenyl, or in which $R^1$ and $R^2$ together represent a hydrocarbon chain which is optionally branched and/or optionally contains a fused benzene ring, characterized in that an aldehyde or ketone of the general formula

in which $R^1$ and $R^2$ have the meanings given above, is reacted with a dichloromethane-phosphonic acid ester of the general formula

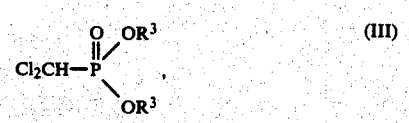

in which $R^3$ individually represents alkyl or phenyl or the two radicals $R^3$ together represent alkanediyl (alkylene), in the presence of a base and if appropriate using a diluent, at a temperature between −50° and +50° C.

It is surprising that 1,1-dichloroalkenes of the formula (I) are obtained, in good yields, considerably more easily and at considerably less expense by the process according to the invention than could be expected from a consideration of the prior art.

It was further surprising that, in this reaction, the sequence in which the reactants are added to one another seems to be important.

Whereas this type of reaction would normally be carried out in such a way that a base is added to the phosphonic acid ester of the formula (III), and the aldehyde or ketone of the formula (II) is then added to the reaction solution, it has been shown that, following this very procedure, the process according to the invention only gives poor results. For this reason, preferred procedures are those in which either the base is added dropwise to a mixture of the compounds (II) and (III), or the compound (III) is added to a mixture of the base and the compound (II).

If, for example, 3-formyl-2,2-dimethyl-cyclopropane-1-carboxylic acid nitrile and dichloromethane-phosphonic acid dimethyl ester are used as the starting materials and sodium methylate is used as the base, the reaction of these compounds can be represented schematically by the following equation:

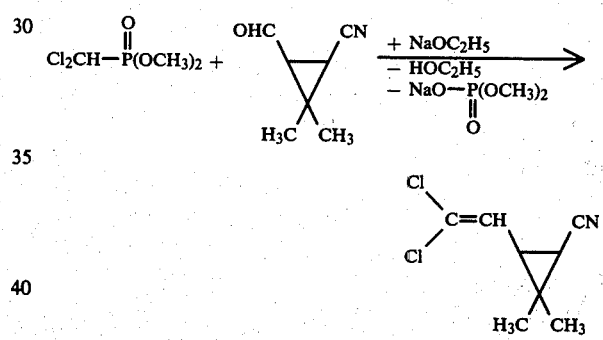

Formula (II) provides a definition of the aldehydes or ketones to be used as starting materials. Preferably, in this formula $R^1$ represents hydrogen, optionally halogen-substituted $C_1$–$C_5$-alkyl, optionally halogen-substituted benzyl, optionally halogen-substituted phenylethyl or phenyl which optionally carries one or more substituents selected from halogen, $C_1$–$C_4$-alkyl, $C_1$–$C_4$-alkoxy, methylenedioxy, cyano and nitro, and $R^2$ represents $C_1$–$C_5$-alkyl which is optionally halogen-substituted, $C_2$–$C_5$-alkenyl, $C_2$–$C_5$-alkynyl, optionally halogen-substituted benzyl, optionally halogen-substituted phenylethyl, phenyl which optionally carries one or more substituents selected from halogen, $C_1$–$C_4$-alkyl, $C_1$–$C_4$-alkoxy, methylenedioxy, cyano and nitro, optionally halogen-substituted styryl or the radical

wherein

Z represents acetyl, cyano or carbamoyl, or $R^1$ and $R^2$ together represent straight-chain or branched alkanediyl with 4 to 10 carbon atoms.

Particularly preferred starting materials are those compounds of the formula (II) in which
$R^1$ represents hydrogen and
$R^2$ represents $C_2$-$C_5$-alkenyl or the radical

wherein

Z represents cyano, acetyl or carbamoyl.

Examples which may be mentioned of starting materials of the formula (II) are: β,β-dimethylacrolein, 3-formyl-2,2-dimethyl-1-cyano-cyclopropane, 3-formyl-2,2-dimethyl-1-carbamoyl-cyclopropane and 3-formyl-2,2-dimethyl-1-acetyl-cyclopropane.

Some of the compounds of the formula (II) are known (see Synthesis 1975, 535–536; and Tetrahedron Lett. 1976, 1,979–1,982). Some of the particularly preferred cyclopropane derivatives of the formula (II) have not hitherto been described in the literature. These compounds are obtained by processes which are in themselves known. One synthesis route is represented schematically in the following scheme (wherein R represents $C_1$-$C_4$-alkyl):

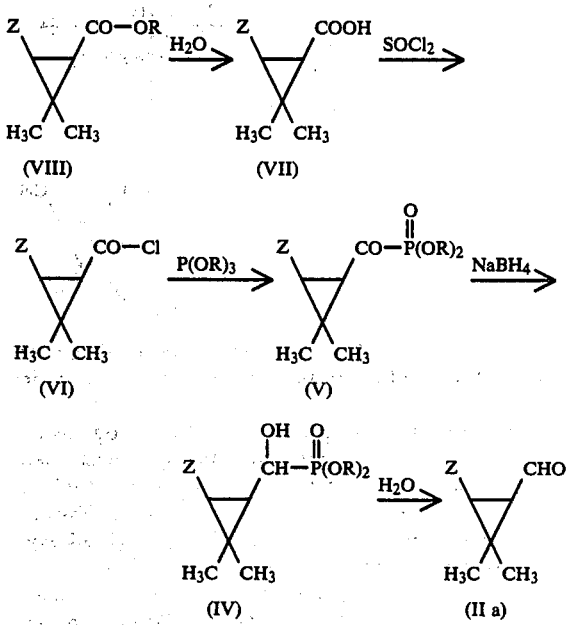

The carboxylic acids of the formula (VII) are obtained by the hydrolysis of known cyclopropanecarboxylic acid esters of the formula (VIII) (see J. Org. Chem. 32, (1967), 3,351–3,355; Bull. Soc. Chim. Belg. 87 (1978), 721–732; and Tetrahedron Lett. 1978, 1,847–1,850), for example by reaction with aqueous-alcoholic potassium hydroxide solution, at a temperature between 20° and 100° C., and subsequent acidification. These carboxylic acids can be converted into the acid chlorides of the formula (VI) by reaction with halogenating agents, for example thionyl chloride, at a temperature between 20° and 80° C.

The cyclopropanoylphosphonic acid esters of the formula (V) are obtained by reacting the acid chlorides (VI) with trialkyl phosphites at a temperature between −20° and +150° C., preferably between 0° and 120° C. (see J. Am. Chem. Soc. 86 (1964), 3,862–3,866; and Methoden der organischen Chemie (Methods of Organic Chemistry) (Houben-Weyl-Müller), 4th edition, volume 12/1, page 453, Georg-Thieme-Verlag, Stuttgart 1963). Distillation under reduced pressure is optionally used to isolate and purify the products.

The α-hydroxy-phosphonic acid esters of the formula (IV) are obtained by reducing the oxo compounds of the formula (V) with sodium tetrahydridoborate, if appropriate using a diluent, for example water or aqueous methanol, at a temperature between −20° and +50° C., and keeping the pH-value at between 5 and 8 by adding a buffer, for example sodium hydrogen phosphate (see Chem. Ber. 103, (1970), 2,984–2,986). Working up is carried out by extracting the reaction mixture with a water-immiscible solvent, for example methylene chloride, drying the extracts, filtering and distilling the solvent off under reduced pressure.

The α-hydroxy-phosphonic acid esters of the formula (IV) can be used to prepare the corresponding aldehydes of the formula (IIa) by treatment with sodium hydroxide solution at a temperature between 0° and 100° C., preferably between 10° and 50° (see Chem. Ber. 103(1970), 2,984–2,986).

As an alternative to the process of preparation outlined above, aldehydes of the formula (IIa) are also obtained by reacting acid chlorides of the formula (VI) with lithium tri-tert.-butoxy-hydridoaluminate (which has optionally been prepared in situ from lithium tetrahydridoaluminate and tert.-butanol) if appropriate in the presence of a diluent, for example tetrahydrofuran, at a temperature between −100° and +100° C., preferably between −80° and +50° C. Working up is carried out by pouring the reaction mixture into a mixture of hydrochloric acid and ice-water and extracting with a water-immiscible solvent, for example diethyl ether. The extracts are dried, filtered and concentrated. Distillation is optionally used to purify the crude product.

Formula (III) provides a definition of the dichloromethane-phosphonic acid esters which are also to be employed as starting materials. Preferably, in this formula;

$R^3$ represents alkyl with 1 to 4 carbon atoms or phenyl, or the two radicals $R^3$ together represent straight-chain or branched alkanediyl (alkylene) with 2 to 5 carbon atoms.

Examples of the compounds (III) which may be mentioned are dichloromethane-phosphonic acid dimethyl ester, diethyl ester and diphenyl ester.

Compounds of the formula (III) are known and can be prepared by processes which are in themselves known (see Synthesis 1975, 535–536; Tetrahedron Lett. 1975, 609–610; and ibid. 1975, 4,409–4,410).

Dichloromethane-phosphonic acid esters of the formula (III) are obtained, for example, by reacting dichloro-methane-phosphonic acid dichloride (see British Pat. No. 707,961) with sodium salts or potassium salts of hydroxy compounds, for example methanol, ethanol, n- and iso-propanol and n-, iso-, sec.- and tert.-butanol, if appropriate in the presence of a diluent, for example toluene, at a temperature between 0° and 50° C. Distillation, optionally after filtration, is used to purify the products.

The process according to the invention is preferably carried out using a diluent. Possible diluents are virtually any of the inert organic solvents, especially aprotic polar solvents. These include ethers, for example glycol dimethyl ether, diglycol dimethyl ether, tetrahydrofuran and dioxane; carboxylic acid amides, for example dimethylforamide, dimethylacetamide and N-methylpyrrolidone; sulphoxides and sulphones, for example dimethylsulphoxide and tetramethylenesulphone; phosphoric acid amides, for example hexamethylphosphoric acid triamide; and nitriles, for example acetonitrile and propionitrile.

The bases which are customary in synthetic organic chemistry can be used in the process according to the invention. These include, as preferences, alkali metal hydroxides, for example sodium hydroxide and potassium hydroxide; alkali metal alcoholates, for example sodium methylate and potassium methylate, sodium ethylate and potassium ethylate, sodium isopropylate and potassium isopropylate and sodium tert.-butylate and potassium tert.-butylate; alkali metal hydrides, for example sodium hydride; alkali metal amides, for example sodium amide; alkyl-lithium compounds, for example butyl-lithium; and amines, for example diazabicyclooctane, diazabicyclononane and diazabicycloundecene. Particularly preferred bases are amines and alcoholates.

The reaction temperature is kept between —about —50° and +50° C., preferably between about —30° and +30° C. The process is generally carried out under normal pressure.

In general, 1 to 1.5 mols, preferably 1 to 1.2 mols, of dichloromethane-phosphonic acid ester of the formula (III), and 1 to 1.5 mols, preferably 1 to 1.2 mols, of base, are employed per mol of 3-formyl-2,2-dimethyl-cyclopropane-1-carboxylic acid ester of the formula (II).

In a preferred embodiment of the process according to the invention, the starting materials of the formulae (II) and (III) are initially introduced in one of the diluents given above, at a temperature between —30° and 0° C., and a solution of the base in one of the diluents given above is added dropwise thereto. The reaction mixture is then left until it reaches room temperature and is subsequently stirred for a few hours. Working up is carried out in the customary manner: the reaction mixture is diluted with water and extraction is carried out with a water-immiscible solvent, for example methylene chloride. The extracts are washed with dilute sodium hydroxide solution and then with water, dried and filtered. The solvent is stripped off from the filtrate, and the product remaining in the residue is purified by vacuum distillation. The NMR spectrum and the boiling point are used for the purpose of characterization.

The 1,1-dichloro-alkenes to be prepared by the process according to the invention can be used as intermediate products for the preparation of insecticidally and acaricidally active pyrethroids (see DE-OS's (German Published Specifications Nos.) 2,621,833, 2,751,610 and 2,810,098).

PREPARATIVE EXAMPLES

EXAMPLE 1

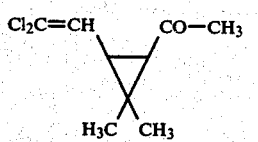
(1)

A solution of 12.3 g (0.11 mol) of potassium tert.-butylate in 30 ml of dimethylformamide was added dropwise, under an inert gas atmosphere (nitrogen or argon) at —20° to —25° C., to a solution of 24 g (0.180 mol) of dichloromethane-phosphonic acid diethyl ester and 14 g (0.1 mol) of 2-acetyl-3,3-dimethylcyclopropanecarboxaldehyde in 100 ml of tetrahydrofuran. The mixture was subsequently stirred for 3 hours without cooling, 200 ml of water were added and extraction was carried out twice with 100 ml of methylene chloride. The organic phase was washed with 50 ml of 10% strength sodium hydroxide solution and then with 3 times 50 ml of water, dried over sodium sulphate and evaporated in vacuo. 14.8 g (71% of theory) of 1-(2,2-dichlorovinyl)-2-acetyl-3,3-dimethylcyclopropane were obtained from the residue, by vacuum distillation, in the form of a pale yellow oil having a boiling point of 55°–57° C./0.3 mbar.

EXAMPLE 2

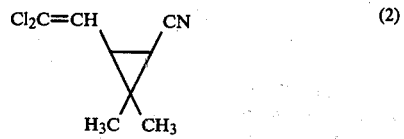
(2)

3-(2,2-Dichloro-vinyl)-2,2-dimethyl-cyclopropane-1-carboxylic acid nitrile could be prepared from 3-formyl-2,2-dimethyl-cyclopropane-1-carboxylic acid nitrile and dichloromethane-phosphonic acid diethyl ester analogously to Example 1. Yield: 33% of theory; boiling point 70° C./0.1 mbar.

EXAMPLE 3

(3)

24.6 g (0.22 mol) of potassium tert.-butylate in 100 ml of tetrahydrofuran were added dropwise, at —15° C., to a solution of 16.8 g (0.2 mol) of dimethylacrolein and 48.6 g (0.22 mol) of dichloromethanephosphonic acid diethyl ester in 200 ml of tetrahydrofuran. When the addition was complete, the reaction temperature was allowed to rise to 20° C. and the mixture was subsequently stirred for 1 hour at this temperature. 500 ml of water were then added to the reaction mixture and extraction was carried out with twice 150 ml of methylene chloride. The combined organic extracts were washed with water, dried over sodium sulphate and fractionated. 26.4 g (87.5% of theory) of 1,1-dichloro-4,4-dimethylbutadiene were obtained in the form of a colorless oil having a boiling point of 52°–54° C./11 mbar.

EXAMPLE 4

(4)

The procedure followed was as in Example 3. However, potassium tert.-butylate was added dropwise in 20 ml of dimethylformamide. 1,1-Dichloro-4,4-dimethylbutadiene was obtained in a yield of 77.5% of theory.

EXAMPLE 5

(5)

The procedure followed was as in Example 3. However, instead of 24.6 g (0.22 mol) of potassium tert.- butylate in 100 ml of tetrahydrofuran being added dropwise at −15° C., 0.22 mol of sodium ethylate in 100 ml of tetrahydrofuran was used for the dropwise addition at a temperature of +15° C. 1,1-Dichloro-4,4-dimethyl-butadiene was obtained in a yield of 48.8% of theory.

The following compounds were also obtained analogously to one of Examples 1 to 5:

| Compound | Formula | Physical constant |
|---|---|---|
| 6 | (Cl)₂C=CH—⟨⟩—Cl | Boiling point 80° C./0.3 mbar |
| 7 | (structure)=C(Cl)₂ | Melting point 134° C. |
| 8 | ⟨⟩=C(Cl)₂ | Boiling point 40° C./0.5 mbar |

Formyl-cyclopropane derivatives of the formula (IIa) to be used as starting materials could be prepared, for example, as follows:

Variant (a)

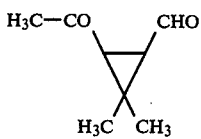

36.6 g (0.495 mol) of tert.-butanol were added dropwise, at 20°–30° C., to a mixture of 6.3 g (0.165 mol) of lithium aluminum hydride and 100 ml of tetrahydrofuran in the course of 1 hour. The mixture was subsequently stirred for 2 hours at room temperature and was then added dropwise, at −50° to −60° C., to a solution of 26.1 g (0.15 mol) of trans-3,3-dimethyl-2-acetyl-cyclopropanecarboxylic acid chloride in 75 ml of tetrahydrofuran. When the addition was complete, the mixture was subsequently stirred for 1 hour, without cooling, and poured onto a mixture of 30 ml of concentrated sodium chloride and 300 g of ice, and extraction was carried out by shaking with twice 400 ml of ether. The organic phases were washed first with 50 ml of saturated sodium bicarbonate solution and then with 100 ml of water, dried over sodium sulphate and evaporated in vacuo. 12.7 g (62% of theory) of trans-3,3-dimethyl-2-acetyl-cyclopropanecarboxaldehyde were obtained, by vacuum distillation of the residue, in the form of a colorless oil having a boiling point of 80°–86° C./10 mbar.

Variant (b)

A mixture of 50 g of α-hydroxy-α-(3-acetyl-2,2-dimethyl-cycloprop-1-yl)-methane-phosphonic acid dimethyl ester, 8 g of sodium hydroxide, 60 ml of water and 200 ml of methylene chloride was stirred for 90 minutes at room temperature. The organic phase was separated off, dried and distilled twice. 20 g (71% of theory) of 3,3-dimethyl-2-acetyl-cyclopropanecarboxaldehyde were obtained in the form of a colorless oil of boiling point 78° C./8 mbar.

α-Hydroxy-phosphonic acid esters of the formula (IV) to be used as starting materials could be prepared, for example, as follows:

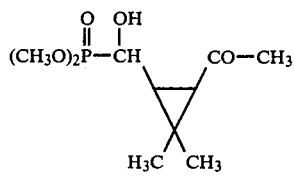

A solution of 50 g (0.2 mol) of α-oxo-α-(3-acetyl-2,2-dimethyl-cycloprop-1-yl)-methanephosphonic acid dimethyl ester in 50 ml of methylene chloride was added dropwise to a mixture, cooled to 0° to 5° C., of 2.5 g of sodium tetrahydridoborate, 100 ml of water and 100 ml of methylene chloride, and the reaction mixture was stirred for two hours at 0° to 5° C. The aqueous phase was then separated off from the organic phase and extracted twice further with methylene chloride. The combined organic phases were dried, filtered and evaporated. After recrystallization of the residual crude product from 200 ml of ethyl acetate/ligroin (2:8), 31 g (62% of theory) of α-hydroxy-α-(3-acetyl-2,2-dimethyl-cycloprop-1-yl)-methanephosphonic acid dimethyl ester of melting point 104° C. were obtained.

The following compound was obtained analogously to the preceding example:

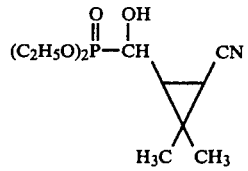

α-Oxo-phosphonic acid esters of the formula (V) to be used as starting materials could be prepared, for example, as follows:

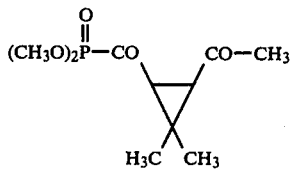

6.5 g (0.05 mol) of trimethyl phosphite were added dropwise to a solution, warmed to 35° to 40° C., of 9 g (0.05 mol) of 3-acetyl-2,2-dimethyl-cyclopropane-1-carboxylic acid chloride in 20 ml of methylene chloride, and the reaction mixture was stirred at 15° to 25° C. for 15 hours. After distilling off the solvent in vacuo, 9 g (72% of theory) of α-oxo-α-(3-acetyl-2,2-dimethyl-cycloprop-1-yl)-methane-phosphonic acid dimethyl ester were obtained.

The following compound was obtained analogously to the preceding example:

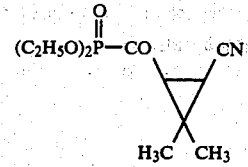

Cyclopropanecarboxylic acid chlorides of the formula (VI) to be used as starting materials could be prepared, for example, as follows:

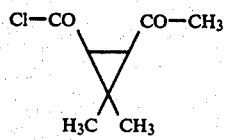

A mixture of 172 g of 3-acetyl-2,2-dimethyl-cyclopropane-1-carboxylic acid, 130 g of thionyl chloride, 2 ml of dimethyl formamide and 200 ml of methylene chloride was heated at the boil for four hours under reflux. After vacuum distillation, 135 g (71% of theory) of 3-acetyl-2,2-dimethyl-cyclopropane-1-carboxylic acid chloride of boiling point 86° C./15 mbar were obtained.

The following compound was obtained analogously:

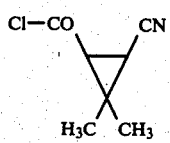

Dichloromethane-phosphonic acid esters of the formula (III) to be used as starting materials could be prepared, for example, as follows:

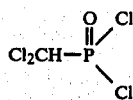
(a)

266 g (2 mol) of aluminum chloride were added in portions to a mixture of 720 g (6 mol) of chloroform and 274 g (2 mol) of phosphorus trichloride. The reaction mixture was then heated at the boil for 12 hours under reflux. The solvent was then stripped off in vacuo and the residue was taken up in 2 liters of methylene chloride. 440 ml of concentrated hydrochloric acid were added dropwise thereto, at 0° C., and the mixture was subsequently stirred for about 2 hours at this temperature. The organic phase was separated off, dried over sodium sulphate and concentrated. The residue was subjected to fractional distillation. 258 g (64.5% of theory) of dichloromethane phosphonic acid dichloride were obtained in the form of a colorless oil of boiling point 48°–50° C./1 mbar.

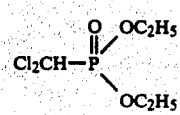
(b)

153.5 g (2.26 mol) of sodium ethylate in 800 ml of ethanol were added dropwise, at 5°–10° C., to a solution of 227.5 g (1.13 mol) of dichloromethane-phosphonic acid dichloride in 800 ml of toluene. The mixture was subsequently stirred at 20° C. for 5 hours. It was then filtered, the filtrate was concentrated and the residue was subjected to fractional distillation. 195 g (78% of theory) of dichloromethane-phosphonic acid diethyl ester were obtained in the form of a colorless oil of boiling point 84° C./1 mbar.

It will be appreciated that the instant specification and examples are set forth by way of illustration and not limitation, and that various modifications and changes may be made without departing from the spirit and scope of the present invention.

We claim:

1. A process for the preparation of a 1,1-dichloroalkene of the formula

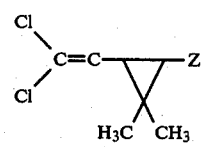

in which

Z is acetyl, cyano or carbamoyl, comprising adding a base selected from the group consisting of NaOCH$_3$, NaOC$_2$H$_5$ and KO—t—C$_4$H$_9$ to a mixture of an aldehyde of the formula

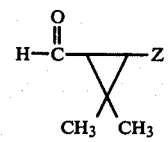

wherein Z is as above defined, and a dichloromethane-phosphonic acid ester of the formula

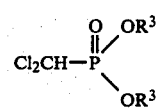

in which

R$^3$ each independently is alkyl with 1 to 4 carbon atoms or phenyl or the two radicals R$^3$ together are alkanediyl with 2 to 5 carbon atoms, and reacting at a temperature between about —50° and +50° C.

2. A process according to claim 1, wherein the base is metered into a mixture of the aldehyde and phosphonic acid ester.

3. A process according to claim 1, wherein the phosphonic acid ester is added to a mixture of the base and aldehyde.

4. A process according to claim 1, wherein the reaction is effected in an aprotic polar organic solvent.

5. A process according to claim 1, wherein the reaction is effected between about —30° and +30° C.

6. A process according to claim 1, wherein about 1 to 1.5 mols of the phosphonic acid ester and about 1 to 1.5 mols of base are employed per mol of the aldehyde.

7. A process according to claim 6, wherein about 1 to 1.2 mols of the phosphonic acid ester and about 1 to 1.2 mols of base are employed per mol of the aldehyde.

8. A process according to claim 1, wherein the base is metered into a mixture of the aldehyde and phosphonic acid ester or the phosphonic acid ester is added to a mixture of the base and aldehyde, the reaction being effected in an aprotic polar organic solvent between about −30° and +30° C. employing about 1 to 1.2 mols of phosphonic acid ester and about 1 to 1.2 mols of base per mol of the aldehyde.

* * * * *